(12) United States Patent
Divo

(10) Patent No.: US 7,438,417 B2
(45) Date of Patent: Oct. 21, 2008

(54) OPHTHALMIC DIAGNOSTIC APPARATUS FOR DIFFERENT TYPES OF TESTS

(75) Inventor: Fabien Divo, Montmorency (FR)

(73) Assignee: Essilor International (Compagnie Generale d'Optique), Charenton le Pont (FR)

(*) Notice: Subject to any disclaimer, the term of this patent is extended or adjusted under 35 U.S.C. 154(b) by 345 days.

(21) Appl. No.: 10/579,915

(22) PCT Filed: Nov. 18, 2004

(86) PCT No.: PCT/FR2004/002942
§ 371 (c)(1),
(2), (4) Date: Jun. 29, 2006

(87) PCT Pub. No.: WO2005/053520
PCT Pub. Date: Jun. 16, 2005

(65) Prior Publication Data
US 2007/0146630 A1    Jun. 28, 2007

(30) Foreign Application Priority Data
Nov. 21, 2003 (FR) .................................. 03 13667

(51) Int. Cl.
A61B 3/00 (2006.01)
A61B 3/02 (2006.01)
(52) U.S. Cl. ............... 351/237; 351/200; 351/239
(58) Field of Classification Search ............ 351/200, 351/222, 224, 237–239
See application file for complete search history.

(56) References Cited

U.S. PATENT DOCUMENTS

| | | | |
|---|---|---|---|
| 4,155,632 A * | 5/1979 | Wolbarsht | 351/243 |
| 4,562,433 A | 12/1985 | Biferno et al. | |
| 4,618,231 A | 10/1986 | Genco et al. | |
| 4,870,486 A | 9/1989 | Nakagawa et al. | |
| 5,331,358 A | 7/1994 | Grimm et al. | |
| 5,416,540 A | 5/1995 | Hayashi | |
| 5,629,798 A | 5/1997 | Gaudreau | |
| 5,823,958 A | 10/1998 | Truppe et al. | |
| 5,907,389 A | 5/1999 | Jiang | |
| 6,367,932 B1 * | 4/2002 | Donaldson | 351/237 |
| 6,474,817 B1 * | 11/2002 | McKinnon et al. | 351/243 |
| 2006/0203195 A1 * | 9/2006 | Squire et al. | 351/211 |

FOREIGN PATENT DOCUMENTS

DE    30 43 511 A1    6/1982

OTHER PUBLICATIONS

Translation of p. 10, line 20, to p. 11, line 12 of DE 30 43 511.

* cited by examiner

Primary Examiner—Jordan M. Schwartz
(74) Attorney, Agent, or Firm—Young & Thompson

(57) ABSTRACT

An ophthalmic diagnostic apparatus, includes a first body (6), for viewing from a given position (4) and a second body (7, 8), for viewing from the position (4), each embodied for display of ophthalmic test patterns, the second body (7, 8) for viewing, being arranged between the first body (6) for viewing and the given position (4). The apparatus further includes a control module (5) for the first and second bodies for viewing, embodied for arranging the bodies in a first configuration in which the second body (7, 8) for viewing is in a condition giving symbols and the first body (6) for viewing is in a plain condition and a second configuration in which the second body (7, 8) for viewing is in a transparent condition and the first body (6) for viewing is in a condition giving symbols.

14 Claims, 2 Drawing Sheets

OPHTHALMIC DIAGNOSTIC APPARATUS FOR DIFFERENT TYPES OF TESTS

The invention relates to ophthalmological diagnostic apparatus.

It relates more particularly to apparatus for effecting tests on a patient for identifying defects of vision such as ametropia, phoria and dyschromatopsia and for effecting measurements such as measurement of the visual acuity of the patient.

This type of apparatus is intended to display various tests adapted to the defects to be detected. The patient is asked what he sees as the tests proceed and the diagnostic is effected as a function of his response.

Thus certain tests are colored (for example tests designed to detect a fusion or color vision defect), others represent large patterns (for example the "Parent dial" for testing astigmatism or measuring phoria), and others in contrast represent very small patterns that must be produced with great accuracy (Landolt rings or other optotypes for high acuity). These tests also vary from country to country.

There is therefore a very large number of these tests which differ in color, size and display accuracy, to the point where it is difficult to produce apparatus adapted to display a large number of different tests with very different characteristics.

In fact, tests based on optotypes of small size, for example conforming to ISO standard 8596, necessitate a high display accuracy whereas other tests, for example astigmatism tests, require the display of large images or color images, without necessitating any particular display accuracy.

On a graphics screen, display accuracy is achieved by a small pixel size, in other words by a high resolution per unit area.

BACKGROUND OF THE INVENTION

There is no commercially available screen having a resolution able to display both tests necessitating accuracy and tests that display large patterns. There are nevertheless various possibilities for displaying different ophthalmological tests. Certain apparatus uses a screenprinted strip on which all the tests are printed, for example. A portion of the strip is displayed in an active window and a mechanical system moves the strip to display the required test in front of the active window.

The above system is a mechanical system for generating virtually all the screening tests and is designed to enable the screenprinted strip to be changed to adapt it to other countries or uses.

Other, similar apparatus uses tests printed on a drum or turntable, rotation of the drum or turntable presenting the test that it is wished to display in an active window.

Other apparatus uses graphics screens, for example of the cathode ray tube (CRT) type or the liquid crystal display (LCD) type. These screens provide very many tests on a single surface without necessitating any mechanical movement. There are therefore many screening software packages for displaying tests on conventional computer screens. The tests are also very easy to modify or to adapt according to the country, as they necessitate only a software modification. The drawback of these systems is that the resolution of the screens is insufficient to obtain both an image of reasonable size and pixels small enough to produce small optotypes with the required accuracy, for example the accuracy required by the ISO standard cited above.

Moreover, other apparatus is limited to displaying predefined patterns on the screen but can display small optotypes very accurately.

SUMMARY OF THE INVENTION

An object of the invention is to use a configurable graphics display to improve the above type of apparatus to enable the display of tests comprising both large patterns and small optotypes.

To this end, the invention is directed to ophthalmic diagnostic apparatus characterized in that it includes a first body to be viewed from a predetermined position and a second body to be viewed from said position, each body being adapted to display ophthalmic test patterns, the second body to be viewed being disposed between the first body to be viewed and the predetermined position, which first body to be viewed has a uniform state and a state for showing signs and which second body to be viewed has a transparent state and a state for showing signs, and in that it further includes a control module for the first and second bodies to be viewed adapted to cause them to assume a first configuration in which the second body to be viewed is in its state for showing signs and the first body to be viewed is in its uniform state and a second configuration in which the second body to be viewed is in its transparent state and the first body to be viewed is in its state for showing signs.

The combination of the first body to be viewed, which is adapted to display large patterns, and the second body to be viewed, which is adapted to display small optotypes, gives the apparatus a dual function.

The two possible states of each of the bodies to be viewed are managed by the control module so that the required configuration may be selected as a function of the type of test.

Thus the different types of tests may be easily and quickly effected within the same apparatus. The specialization of each body to be viewed also means that the bodies can be optimized for their respective application and produced at lower cost.

In a preferred embodiment of the invention, the apparatus may further have the features listed hereinafter, separately or in combination:

- the first body to be viewed includes a first graphics screen;
- the second body to be viewed includes a second graphics screen;
- one of the bodies to be viewed has a higher resolution per unit area than the other body to be viewed;
- the body to be viewed having the higher resolution is disposed between the other body to be viewed and said position;
- the first graphics screen and the second graphics screen are substantially parallel;
- the first graphics screen and the second graphics screen are superposed;
- the first graphics screen is a color screen and the second graphics screen is a liquid crystal display;
- the second graphics screen includes a liquid crystal display etched with predefined ophthalmic test patterns;
- the second body to be viewed includes a second graphics screen and a reflecting body adapted to reflect the second graphics screen;
- a first graphics screen belonging to the first body to be viewed is perpendicular to the second graphics screen belonging to the second body to be viewed and the reflecting body includes a semitransparent sheet disposed obliquely to the two graphics screens; and
- the second graphics screen has a smaller area than the first graphics screen.

BRIEF DESCRIPTION OF THE DRAWINGS

Other features and advantages of the invention will emerge in the light of the following description of a nonlimiting preferred embodiment of the invention, which description is given with reference to the appended drawings, in which.

DETAILED DESCRIPTION OF THE PREFERRED EMBODIMENTS

Figure 1:
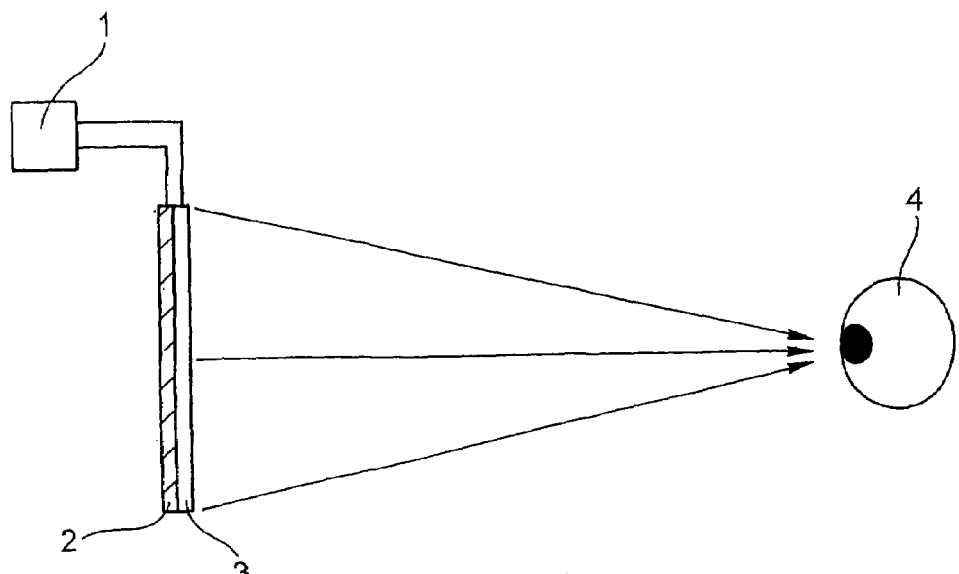
FIG. 1 is a diagram representing from the side the eye of a patient viewing a first embodiment of diagnostic apparatus of the invention.

FIG. 1 represents diagrammatically the main components of ophthalmic diagnostic apparatus. A control module 1 is connected to a first graphics screen 2 and to a second graphics screen 3. In this first embodiment, the graphics screens 2, 3 are superposed to form a display adapted to display many types of tests, including tests in color, and to display tests requiring high accuracy, without mechanical movement.

The first graphics screen 2 is a color graphics screen of the LCD, CRT or equivalent type, of moderate resolution, for example 800 rows by 600 columns in the case of a 15" screen. This screen is used to display tests necessitating colors, such as phoria tests, fusion tests, duochrome tests, Hishiara tests. It is also used to display other types of tests, for example tracking tests, acuity tests (for relatively low acuity) and astigmatism tests.

These various tests have the common feature of not necessitating a high display resolution. The graphics screen 2 may therefore consist of an ordinary computer display of relatively low cost.

The second graphics screen 3 is used to display tests requiring high accuracy, which is not possible on the first graphics screen 2, for example acuity tests for high acuities.

In this configuration, the second graphics screen 3 is a transmission type liquid crystal display screen the same size as the first graphics screen 2. Patterns 9 corresponding to high acuity optotypes are etched directly onto the liquid crystal display screen during manufacture. Thus they do not consist of pixels and appear when a region of the liquid display screen having a predetermined shape is activated. Each optotype may be lit independently of the others.

When the liquid crystals of the second graphics screen 3 are not excited, the screen 3 remains transparent.

The control module 1, consisting of a computer and appropriate software, for example, provides a first function of display as such. It is used to display on the first screen 2 certain tests selected by the user and is also used to display on this first screen 2 a uniform surface, for example a white background.

The control module 1 is adapted to activate and deactivate each of the liquid crystal cells constituting the second screen 3 to cause certain of the optotypes etched therein to appear or to render this second screen 3 completely transparent by deactivating all the cells.

The control module 1 also has a second function of coordinating the displays on the first screen 2 and the second screen 3. The control module 1 is in fact adapted to offer a first display configuration in which the first screen 2 is commanded to display test patterns, the second screen 3 remaining transparent, and a second display configuration in which the first screen 2 is commanded to display a uniform white image and the second screen 3 displays etched optotypes.

In the first display configuration, the eye 4 of a patient viewing the diagnostic apparatus sees only the tests displayed by the first screen 2.

In the second display configuration, the tests displayed by the second screen 3 appear by virtue of their contrast with the background that the first screen 2 constitutes. The latter is preferably lit when it is in its uniform state, as here. What the eye 4 sees in this configuration is represented in FIG. 2, which shows the two superposed screens 2, 3, the cross-hatching of the first screen 2 showing that the latter is in its "white screen" configuration whereas on the second screen 3 optotypes (here broken circles 9) appear in the foreground relative to the white background.

Figure 3:
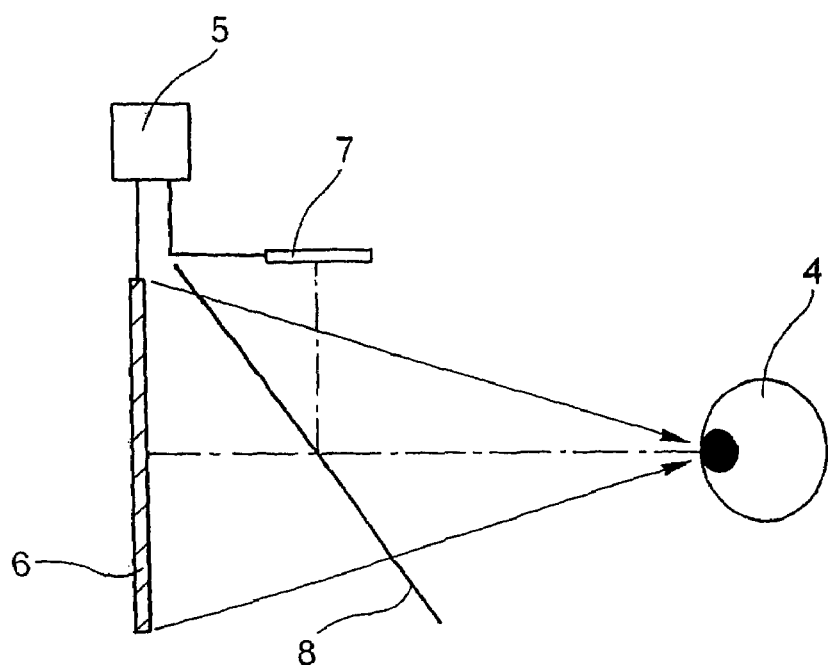
FIG. 3 is a view similar to FIG. 1 representing a second embodiment of diagnostic apparatus of the invention.
Figure 4:
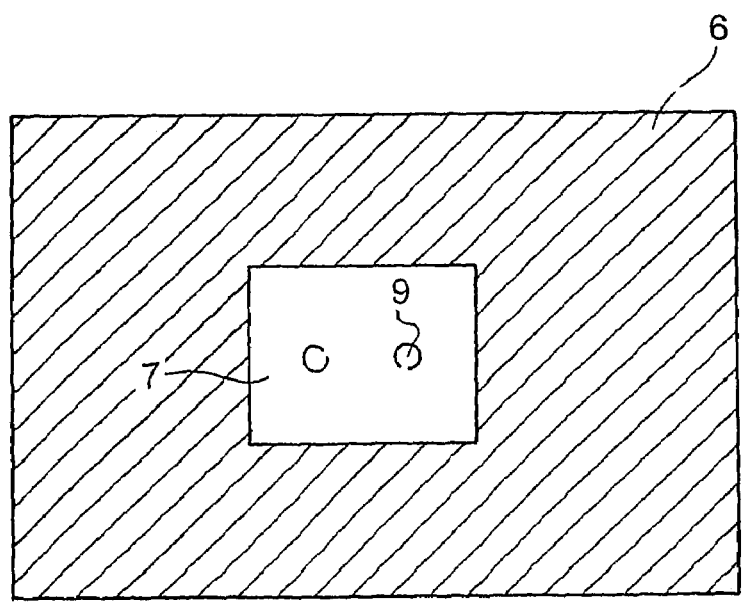
FIG. 4 is a view similar to FIG. 2 representing the second embodiment of diagnostic apparatus of the invention.

FIGS. 3 and 4 correspond to a second embodiment of the invention.

The ophthalmic diagnostic apparatus also includes a control module 5 connected to a first graphics screen 6 and to a second graphics screen 7. The graphics screens 6, 7 are disposed perpendicularly to each other and a semi-transparent sheet 8 is inserted obliquely between the two screens 6, 7 at an angle of approximately 45° to each of the screens 6, 7.

Figure 2:
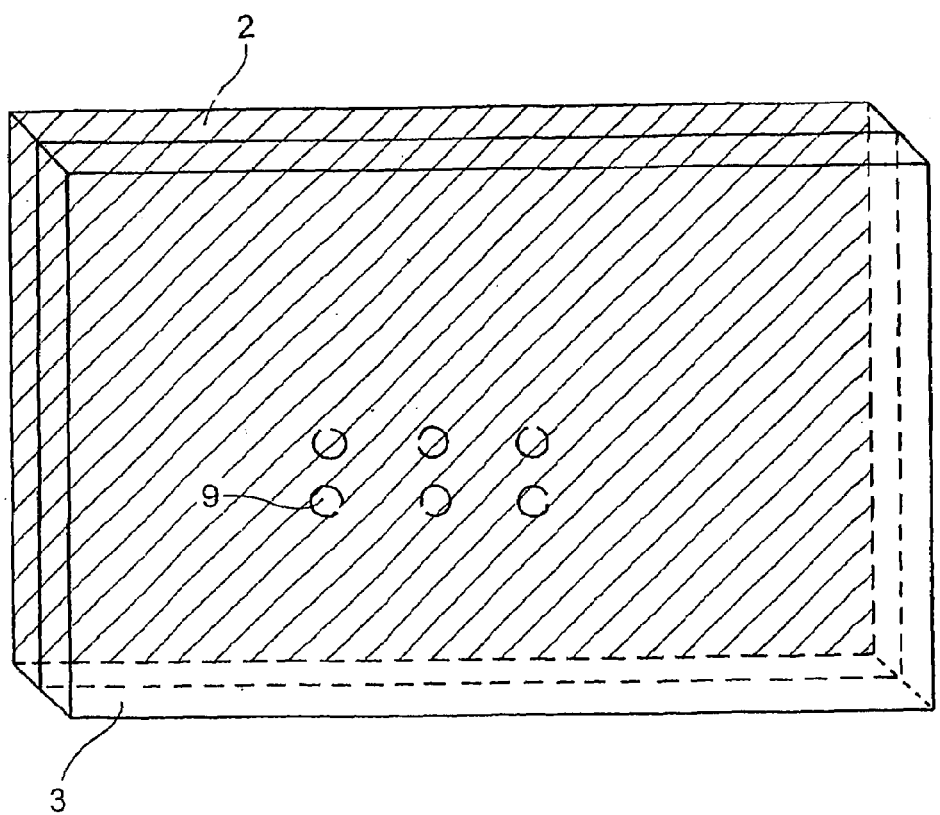
FIG. 2 represents the image viewed by the patient in FIG. 1.

The first graphics screen 6 is similar to the first graphics screen 2 of the first embodiment shown in FIGS. 1 and 2. The second graphics screen 7 is a screen of substantially the same resolution as the first screen 6 but of much smaller size, so that the second screen 7 has a resolution per unit area higher than that of the first screen 6 (i.e. the minimum size of a pixel of the second screen 7 is less than the minimum size of a pixel of the first screen 6).

Here the control module 5 is also adapted to assume a first configuration in which the first screen 6 is activated and displays test patterns and the second screen 7 is turned off. The semitransparent sheet 8, which has the properties of an unsilvered mirror, allows the eye 4 of the patient to see the first screen 6 but does not reflect an image of the second screen 7 that is turned off.

In a second configuration of the control module 5, in which the eye 4 of the patient sees the image represented in FIG. 4, the first screen 6 is turned off and the second screen 7 is activated to display optotypes 9. Because of the semitransparent sheet 8, the eye 4 perceives only the patterns on the second screen 7 reflected from the surface of the sheet 8. An alternative in this second configuration is for the first screen 6 also to be lit. In this case, only the portion of the screen 6 on which the reflected image of the screen 7 is not superposed must be lit.

The ophthalmic diagnostic apparatus of which first and second embodiments have now been described is used in the manner indicated hereinafter.

The apparatus includes a first graphics screen 2, 6 produced at lower cost and the characteristics whereof (resolution per unit area) are adapted to display a large number of ophthalmic test patterns selected by the user by means of a software interface.

The second graphics screen 3, 7 is adapted to display tests that have to be produced with great accuracy.

The two screens 2, 3, 6, 7 are physically or optically superposed and are coordinated by a control module 1, 5 that renders one of the screens active while the other remains inactive. The user can select directly which configuration of the control module 1, 5 is the most suitable. The control module 1, 5 can moreover select automatically the configuration appropriate to the test selected by the user.

The invention claimed is:

1. Ophthalmic diagnostic apparatus characterized in that it includes a first body (2, 6) to be viewed from a predetermined position (4) and a second body (3, 7, 8) to be viewed from said position (4), each body being adapted to display ophthalmic test patterns, the second body (3, 7, 8) to be viewed being disposed between the first body (2, 6) to be viewed and the predetermined position (4), which first body (2, 6) to be viewed has a uniform state and a state for showing signs and which second body (3, 7, 8) to be viewed has a transparent state and a state for showing signs, and in that it further includes a control module (1, 5) for the first and second bodies to be viewed adapted to cause them to assume a first configuration in which the second body (3, 7, 8) to be viewed is in its state for showing signs and the first body (2, 6) to be viewed is in its uniform state and a second configuration in which the second body (3, 7, 8) to be viewed is in its transparent state and the first body (2, 6) to be viewed is in its state for showing signs.

2. Apparatus according to claim 1, characterized in that the first body to be viewed includes a first graphics screen (2, 6).

3. Apparatus according to claim 1, characterized in that the second body to be viewed includes a second graphics screen (3, 7).

4. Apparatus according to claim 1, characterized in that one of the bodies to be viewed has a higher resolution per unit area than the other body to be viewed.

5. Apparatus according to claim 4, characterized in that the body to be viewed having the higher resolution is disposed between the other body to be viewed and said position.

6. Apparatus according to claim 3, characterized in that the first graphics screen (2) and the second graphics screen (3) are substantially parallel.

7. Apparatus according to claim 6, characterized in that the first graphics screen (2) and the second graphics screen (3) are superposed.

8. Apparatus according to claim 6, characterized in that the first graphics screen is a color screen (2) and the second graphics screen is a liquid crystal display (3).

9. Apparatus according to claim 8, characterized in that the second graphics screen includes a liquid crystal display (3) etched with predefined ophthalmic test patterns (9).

10. Apparatus according to claim 1, characterized in that the second body to be viewed includes a second graphics screen (7) and a reflecting body (8) adapted to reflect the second graphics screen (7).

11. Apparatus according to claim 10, characterized in that a first graphics screen (6) belonging to the first body to be viewed is perpendicular to the second graphics screen (7) belonging to the second body to be viewed and the reflecting body includes a semitransparent sheet (8) disposed obliquely to the two graphics screens (6, 7).

12. Apparatus according to claim 11, characterized in that the second graphics screen (7) has a smaller area than the first graphics screen (6).

13. Apparatus according to claim 2, characterized in that the second body to be viewed includes a second graphics screen (3, 7).

14. Apparatus according to claim 7, characterized in that the first graphics screen is a color screen (2) and the second graphics screen is a liquid crystal display (3).

* * * * *